United States Patent
Eck et al.

(10) Patent No.: US 9,255,827 B2
(45) Date of Patent: *Feb. 9, 2016

(54) COMPUTER BASED FLUID FLOW VELOCITY ESTIMATION FROM CONCENTRATIONS OF A REACTING CONSTITUENT FOR PRODUCTS AND SERVICES

(71) Applicant: International Business Machines Corporation, Armonk, NY (US)

(72) Inventors: Bradley Eck, Dublin (IE); Sergiy Zhuk, Dublin (IE)

(73) Assignee: International Business Machines Corporation, Armonk, NY (US)

(*) Notice: Subject to any disclaimer, the term of this patent is extended or adjusted under 35 U.S.C. 154(b) by 123 days.

This patent is subject to a terminal disclaimer.

(21) Appl. No.: 14/141,016

(22) Filed: Dec. 26, 2013

(65) Prior Publication Data

US 2015/0168199 A1 Jun. 18, 2015

Related U.S. Application Data (63) Continuation of application No. 14/109,407, filed on Dec. 17, 2013.

(51) Int. Cl.
  *G01F 1/86* (2006.01)
  *G01F 1/704* (2006.01)
  (Continued)

(52) U.S. Cl.
  CPC ............... *G01F 1/704* (2013.01); *G01F 1/712* (2013.01); *C07C 37/20* (2013.01); *C07C 39/16* (2013.01); *G01F 1/667* (2013.01); *G01F 1/708* (2013.01); *G01F 1/74* (2013.01); *G01F 1/76* (2013.01); *G01F 1/86* (2013.01); *G01N 23/04* (2013.01); *G01N 23/12* (2013.01); *G01T 1/247* (2013.01)

(58) Field of Classification Search
  CPC ........ G01N 23/12; G01N 23/04; G01T 1/247; G01F 1/704; G01F 1/712; G01F 1/74; G01F 1/86; G01F 1/76; G01F 1/667; C07C 37/20; C07C 39/16
  USPC ................................. 702/45; 73/861.04, 19.1
  See application file for complete search history.

(56) References Cited

U.S. PATENT DOCUMENTS 3,975,947 A * 8/1976 Kruishoop .................... 73/61.59
4,554,832 A * 11/1985 Hasegawa et al. ............. 73/19.1
(Continued)

FOREIGN PATENT DOCUMENTS

EP 1653227 A1 5/2006
EP 2116837 A1 11/2009

OTHER PUBLICATIONS

Biswas et al., "A Model for Chlorine Concentration Decay in Pipes", Wat. Res. vol. 27, No. 12, 1993, pp. 1715-1724.
(Continued)

*Primary Examiner* — Carol S Tsai
(74) *Attorney, Agent, or Firm* — Cantor Colburn LLP (57) ABSTRACT

A method for estimating a fluid flow velocity may include receiving, with a processing device, a plurality of observations corresponding to a concentration of a constituent of a flowing fluid mixture, and computing a final estimate of an average velocity of the flowing fluid mixture based at least in part on the observations, wherein the constituent is undergoing a chemical reaction and the computing implements a reactive transport model.

6 Claims, 3 Drawing Sheets

(51) Int. Cl.
*G01F 1/712* (2006.01)
*G01F 1/76* (2006.01)
*C07C 39/16* (2006.01)
*G01T 1/24* (2006.01)
*G01N 23/04* (2006.01)
*G01N 23/12* (2006.01)
*G01F 1/66* (2006.01)
*G01F 1/74* (2006.01)
*C07C 37/20* (2006.01)
*G01F 1/708* (2006.01)

(56) References Cited

U.S. PATENT DOCUMENTS

| | | | | |
|---|---|---|---|---|
| 5,248,839 | A * | 9/1993 | Iimuro et al. | 568/727 |
| 5,396,806 | A * | 3/1995 | Dechene et al. | 73/861.04 |
| 5,594,179 | A | 1/1997 | Marsh | |
| 6,239,600 | B1 * | 5/2001 | Suzuki et al. | 324/637 |
| 7,299,140 | B2 * | 11/2007 | Liu et al. | 702/45 |
| 7,707,897 | B2 * | 5/2010 | Ong | 73/861.04 |
| 2004/0217067 | A1 | 11/2004 | Meredith et al. | |
| 2010/0285612 | A1 | 11/2010 | Iwasaki et al. | |
| 2011/0029261 | A1 | 2/2011 | Muta et al. | |
| 2013/0006130 | A1 * | 1/2013 | Olde et al. | 600/504 |
| 2014/0241110 | A1 * | 8/2014 | Igata, Eishi | 366/340 |
| 2015/0160055 | A1 * | 6/2015 | Polikhov et al. | 378/62 |

OTHER PUBLICATIONS

Dertinger et al, "Generation of Gradients Having Complex Shapes Using Microfluidic Networks", Analytic Chemistry, vol. 73(6), pp. 1240-1246, 2001.

Ozdemir et al., "Unsteady 2-D Chlorine Transport in Water Supply Pipes", Wat. Res. vol. 33, No. 17, 1999, pp. 3637-3645.

Powell et al., "Factors Which Control Bulk Chlorine Decay Rates", Wat. Res. vol. 34, No. 1, 2000, pp. 117-126.

S.M. Zhuk, "State Estimation for a Dynamical System Described by a Linear Equation with Unknown Parameters," Ukrainian Mathematical Journal, vol. 61, No. 2, 2009, pp. 1-22.

Baker, "Flow Measurement Handbook: Industrial Designs, Operating Principles, Performance, and Applications", Cambridge University Press, 2000, pp. 1-30.

* cited by examiner

COMPUTER BASED FLUID FLOW VELOCITY ESTIMATION FROM CONCENTRATIONS OF A REACTING CONSTITUENT FOR PRODUCTS AND SERVICES

CROSS-REFERENCE TO RELATED APPLICATIONS

The present application is a Continuation of U.S. patent application Ser. No. 14/109,407, entitled "COMPUTER-BASED FLUID FLOW VELOCITY ESTIMATION FROM CONCENTRATIONS OF A REACTING CONSTITUENT FOR PRODUCTS AND SERVICES", filed on Dec. 17, 2013, which is incorporated herein by reference in its entirety.

BACKGROUND

The present invention relates generally to fluid dynamics, and more specifically, to estimating the average velocity of a flowing fluid mixture from observed concentrations of a reacting constituent of the fluid.

A variety of devices and methods are available for measuring the volumetric flow rate of a fluid are available. Typical flow measurement devices include turbine meters, venturi meters, orifice plate meters, pressure drop measurements, ultrasonic meters, and flumes, among others. Flow measurement devices often are inserted into a pipe or flow channel. Such invasive techniques are inconvenient and expensive.

Some existing flow meters determine the flow rate of a fluid based on a comparison of the static pressure and the dynamic pressure of the fluid at a given location. Other flow meters are available that estimate the flow rate of a fluid based on a relationship between the fluid temperature and the kinematic viscosity of the fluid.

Still other fluid flow meters are available that determine the travel time of exhaust gas between two points by measuring the fluctuating concentration of a component gas in the exhaust flow at each of the two points. The exhaust gas velocity may be calculated based on the distance between the two points and the time required for the exhaust gas to travel between the two points.

Fluid flow control systems are available that use a reactive transport model to determine a desired flow rate in a fluid flow control system. A typical flow control system of this type uses a reaction-diffusion equation and a conservation of mass equation to model the chlorine concentration profile along a contact basin in order to determine the appropriate flow rate the system that will result in a desired concentration of chlorine in a location of the basin at a particular point in time.

In addition, fluid constituent concentration measuring instruments are available that use fluid temperature and flow rate as inputs to determine an applicable impedance change per unit time—particulate concentration constant from a predetermined table, which may be obtained in advance by experiment or calculated.

Some existing water distribution systems include relatively few sensors. This sparsity is especially prevalent for flow meters, because these often are expensive to install and costly to maintain. Flow meters often are available only at the inlet to a relatively expansive metered area of a distribution system. Even in cases where individual consumers have flow meters, sampling rates generally have low temporal resolution. The general lack of available flow measurement makes it difficult to evaluate usage and locate leakage. Nevertheless, in many water distribution systems, measurements of water quality parameters, such as chlorine concentration, have become more common.

SUMMARY

According to one embodiment of the present invention, a method for estimating a fluid flow velocity includes receiving, with a processing device, a plurality of observations corresponding to a concentration of a constituent of a flowing fluid mixture, and computing a final estimate of an average velocity of the flowing fluid mixture based at least in part on the observations, wherein the constituent is undergoing a chemical reaction and the computing implements a reactive transport model.

According to another embodiment of the present invention, a system for estimating a fluid flow velocity includes an assimilative flow estimator configured to receive a plurality of observations corresponding to a concentration of a constituent of a flowing fluid mixture and compute a final estimate of an average velocity of the flowing fluid mixture based at least in part on the observations, wherein the constituent is undergoing a chemical reaction and the computing implements a reactive transport model.

According to yet another embodiment of the present invention, a computer program product for estimating a fluid flow velocity includes a computer readable storage medium having program code embodied therewith, the program code executable by a computer to implement receiving a plurality of observations corresponding to a concentration of a constituent of a flowing fluid mixture, and computing a final estimate of an average velocity of the flowing fluid mixture based at least in part on the observations, wherein the constituent is undergoing a chemical reaction and the computing implements a reactive transport model.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Embodiments of the present invention provide systems and methods to infer the average velocity of a flowing fluid mixture from observed concentrations of a reacting constituent of the fluid. In many real-world fluid-handling systems, the volumetric flow rate of the fluid as well as the concentration of one or more constituents of the fluid are of interest. Conventionally, flow rate and constituent concentrations have been individually estimated by separate, dedicated measurement devices. By inferring the fluid flow rate from observed concentrations of a reacting constituent of the fluid, an embodiment of the present invention may provide an estimate of the volumetric flow rate without necessitating a dedicated flow measurement device.

An embodiment provides a method for estimating the velocity of a flowing fluid. A prerequisite condition for the method requires that the fluid include a constituent substance undergoing a chemical reaction in a system of interest. The method may include collecting multiple observations, or measurements, of the concentration of the constituent substance in the fluid mixture in the system. The observations may be taken from one or more sensors at a single location or at multiple locations in the path of the fluid flow. The method may further include producing or receiving an estimate of the accuracy of the individual concentration measurements.

The method may develop an initial, or a priori, estimate of the volumetric flow rate of the fluid in the system of interest. The method may further assimilate the concentration observations, as well as the a priori flow rate estimate, into a reactive transport model that models the constituent in the system, and obtain an a posteriori estimate of the fluid velocity and corresponding volumetric flow rate using the reactive transport model.

An embodiment may provide a relatively inexpensive technique for modeling flow rate using readily available measurements of constituent concentrations, enabling flow rate estimates to be made at more locations in a system. Estimating flow rates at additional locations may increase the accuracy of network simulation models, for example, enabling leak detection, which may improve network management and operation.

An embodiment provides a system for estimating the velocity of a flowing fluid. The system may receive concentration measurements of a reacting substance in the fluid mixture as input. The system may implement a parametric description of the reaction process and a linear transport model that describes the transport of the reacting substance by the fluid flow. The system may employ numerical techniques for solving partial differential equations, such as finite differencing, along with minimax data assimilation to provide estimated fluid flow velocity, as well as uncertainty characteristics for the estimated flow.

Figure 1:
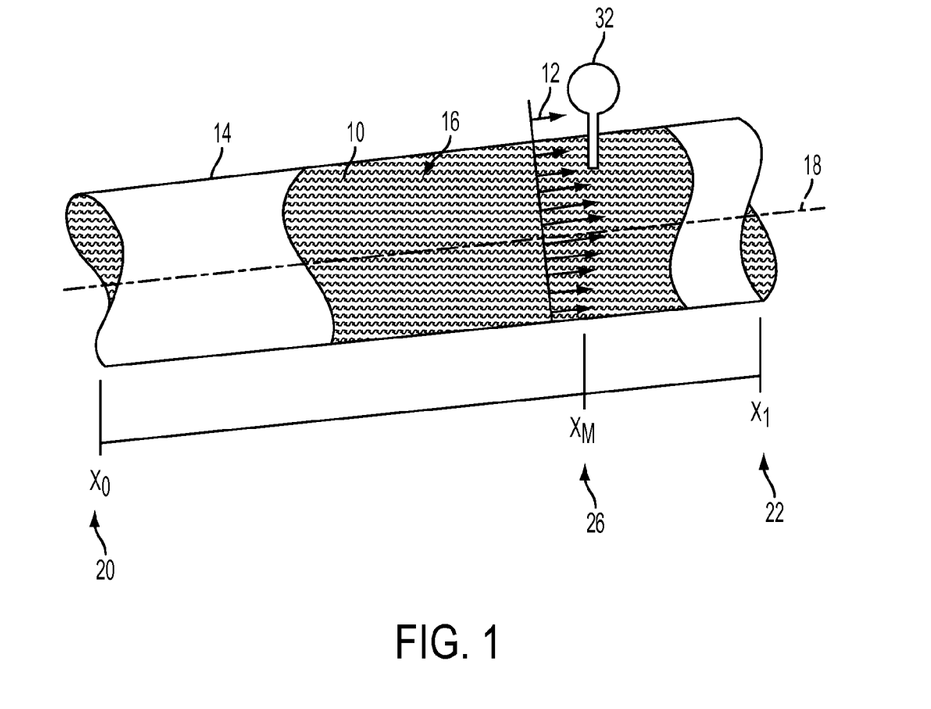
FIG. 1 is a partial cutaway drawing of an apparatus in accordance with an embodiment of the invention.

With reference now to FIG. 1, a fluid 10 flowing at an average velocity, $u_m$, 12 in a conduit 14 is shown. The fluid 10 may contain a mixture or solution including a constituent substance 16 undergoing a chemical reaction. In an embodiment, the conduit 14 may include a closed conduit, such as a pipe or a tunnel, as shown in FIG. 1. In an alternative embodiment, the conduit 14 may include an open conduit, such a channel, a stream or a river.

The conduit 14 may extend generally along an axis 18, or path of flow, at least from a proximal reference point, $x_0$, 20 to a distal reference point $x_1$, 22. Of course, a person of ordinary skill in the art will readily apprehend that the conduit 14 need not extend straight along the axis 18, but rather, it will suffice that an average distance traveled by the flowing fluid 10 may be estimated along the path of flow.

Figure 2:
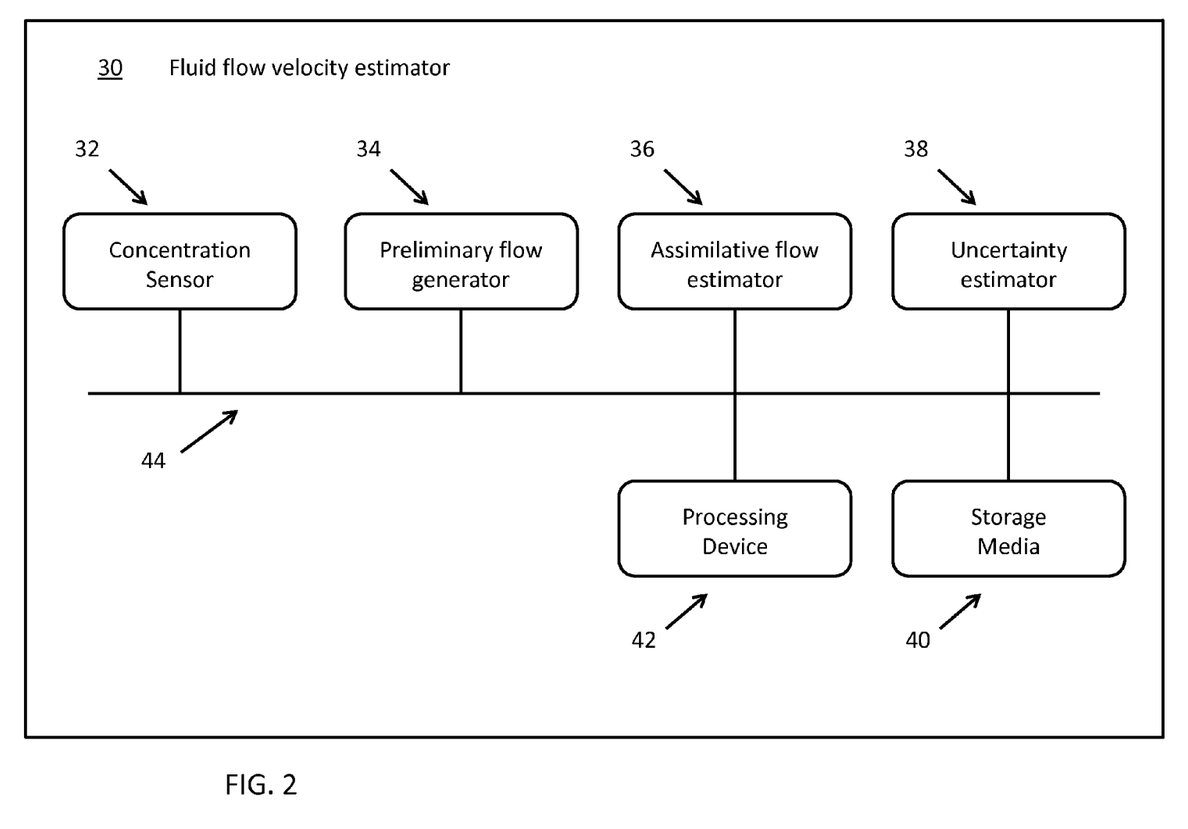
FIG. 2 is a schematic diagram of an apparatus in accordance with an embodiment of the invention.

Referring now to FIG. 2, a fluid flow velocity estimator 30 in accordance with the present invention may infer the average velocity of a flowing fluid mixture from observed concentrations of a reacting constituent of the fluid 10. The fluid flow velocity estimator 30 may include a concentration sensor 32, a preliminary flow generator 34, an assimilative flow estimator 36, uncertainty predictor 38, storage media 40 and a processing device 42, all of which may be communicatively connected by data links 44.

The concentration sensor 32 may be communicatively coupled to the conduit 14, for example, at a location, $x_m$, 26 along the length of the conduit 14, as shown in FIG. 1. In an embodiment, the concentration sensor 32 may be introduced into the conduit 14 by way of an existing fixture, fitting or orifice that has been communicatively coupled to the conduit 14 for another purpose. The concentration sensor 32, may be configured to take one or more measurements, or observations, of the concentration of the constituent substance 16. The concentration sensor 32 may send the concentration observations to the assimilative flow estimator 36.

The preliminary flow generator 34 may develop an a priori estimate of the flow rate. For example, the preliminary flow generator 34 may receive as input known information regarding the fluid flow system, such as the conduit size or diameter, a historical flow rate, the number of homes or size of community serviced, or the like, and create an estimate of the volumetric flow rate of the system and corresponding average fluid flow velocity 12 in the conduit 14. The preliminary flow generator 34 may send the a priori estimate to the assimilative flow estimator 36. In an alternate embodiment, the fluid flow velocity estimator 30 may be configured to receive the a priori flow rate or velocity estimate as an input.

The assimilative flow estimator 36 may be configured to receive the concentration observations, or measurements, of the constituent substance 16 from the concentration sensor 32. For example, the assimilative flow estimator 36 may receive a time-series of sequential concentration observations taken at location $x_m$ 26.

The assimilative flow estimator 36 may implement a reactive transport model, including one or more partial differential equations, that relates constituent concentrations at a location and time with a corresponding fluid flow velocity and other parameters. In an embodiment, an uncertain forcing term and uncertain transport coefficients may reflect limited knowledge regarding the fluid velocity. In an embodiment, the reactive transport model may be implemented in forward and/or backward in time.

In an alternative embodiment, the assimilative flow estimator 36 may receive the relevant reactive transport model as an input. The assimilative flow estimator 36 may assimilate the concentration observations, as well as the a priori estimate, into the reactive transport model and find a solution to the partial differential equations in order to estimate the average velocity 12 of the fluid 10 in the conduit 14.

As an example of a specific application of the fluid flow velocity estimator 30, chlorine concentration in a single pipe may be exemplified. A chlorine probe at a particular location along the pipe may record chlorine concentrations in the pipe, for example, at 15-minute time intervals. The objective is to infer the time-series flow rate, or the corresponding flow velocity, from the observed series of chlorine concentrations.

The behavior of chlorine concentration in water systems is well-studied and is affected by several mechanisms, including chemical reaction, radial diffusion, and axial advection. The principle mechanism is reaction. Thus, although the concentration across the pipe varies to some extent as a result of decay, a one-dimensional reactive transport model may be used for water quality simulation:

$$\frac{\partial C(x,t)}{\partial t} = -u(t)\frac{\partial C(x,t)}{\partial x} + K(u(t))C(x,t) \qquad (1)$$

where C is the chlorine concentration at the location in the pipe, u is the fluid flow velocity, t represents time, and the concentration decays according to the first order constant, K.

In this case, a numerical solution is preferable, because a direct analytical solution to the partial differential equation is not readily available. For example, a finite-difference approach may be employed with upwinded differences used in space. Implementing a simple uniform grid in space and the Crank-Nicolson implicit scheme in time with upwinded difference expressions and third order approximates yields the following approximated spatial derivatives:

$$\frac{\partial C_i}{\partial x} = \frac{2C_{i-2} - 6C_{i-1} + 3C_i + 2C_{i+1+}}{6\Delta x} \qquad (2a)$$

where two upwind points are available (that is, i=3 ... N−1);

$$\frac{\partial C_i}{\partial x} = \frac{-2C_{i-1} - 3C_i + 6C_{i+1+} - C_{i+2}}{6\Delta x} \qquad (2b)$$

where only one upwind point is available (that is, i=2);

$$\frac{\partial C_i}{\partial x} = \frac{-2C_{i-3} + 9C_{i-2} - 18C_{i-1} + 11C_i}{6\Delta x} \qquad (2c)$$

where no downstream points are available (at the last point in the domain). This results in a linear system of equations that can be solved to estimate the velocity of the fluid flow in the pipe. Of course, a person of ordinary skill in the art will recognize that the partial differential equations may be modified to create reactive transport models for systems that are more complex than a single pipe.

The uncertainty estimator 38 may be configured to receive information about the observation noise, for example, from a database in the storage media 40. For example, in an embodiment, the uncertainty estimator 38 may receive a statistical uncertainty description in the form of ellipsoidal bounding sets. In an embodiment, the bounding sets may be represented by symmetric positive definite matrices of appropriate dimensions. The uncertainty estimator 38 may create a statistical uncertainty estimate regarding the estimated fluid flow.

The storage device 40 may include any type of computer memory medium organized in any format, such as, for example, a relational model database server, a hierarchical database, an information management system, a virtual storage access method server, a hard disk drive (HDD), a magnetic tape, a disk drive, a compact disk (CD) drive, an integral or removable solid-state drive (SSD), or any other suitable memory medium known in the art.

The processing device 42 may include any computer processing device capable of numerical analysis, as required. For example, in any embodiment, the processing device 42 may be implemented using a mainframe computer, a server, a desktop personal computer, a laptop computer, a notebook computer, a tablet computing device, a mobile computing device, or any other suitable computer processing device. In any embodiment, the processing device 42 may further include one or more memory devices, including but not limited to read-only memory (ROM), random access memory (RAM), or a cache memory; one or more input/output (I/O) devices, including but not limited to a monitor, a keyboard, or a pointing device; one or more storage devices, including but not limited to a hard disk drive (HDD), a compact disk (CD) drive, an integral or removable solid-state memory device (SSD); a network connection interface; as well as other integral, peripheral or accessory computer components as are known in the art.

The analog or digital data links 44 may include any connective medium capable of transmitting analog or digital data, as the specific application may require. For example, in any embodiment, the data links 44 may be implemented using any type of combination of known communications connections, including but not limited to digital data buses, a universal serial bus (USB), an Ethernet bus or cable, a wireless access point, twisted pairs of wires, or the like. In any embodiment, any portion or all of the data links 44 may be implemented using physical connections, radio frequency or wireless technology. A person of ordinary skill in the art will readily apprehend that any combination of numerous existing or future data communication technologies may be implemented in association with an embodiment of the invention.

Figure 3:
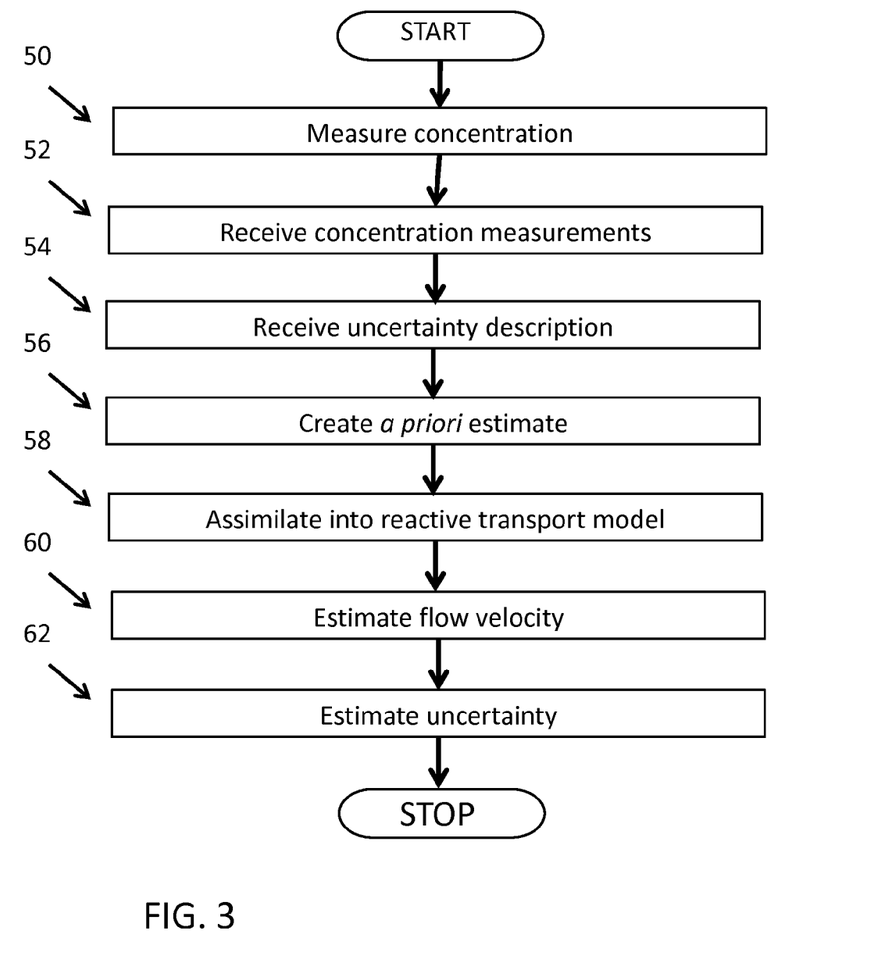
FIG. 3 is a flow diagram of a method in accordance with an embodiment of the invention.

Referring now to FIG. 3, a method of inferring the average velocity of a flowing fluid mixture from observed concentrations of a reacting constituent of the fluid in accordance with the present invention is generally shown. In block 50, concentration measurements, or observations, may be collected for the point of interest. For example, a time series of observations may be taken using a concentration sensor.

In block 52, the concentration measurements may be received, for example, by an interface of the fluid flow velocity estimator of FIG. 2 receiving data-sets as input. The data-sets may include concentrations of the constituent of interest over a period of time. In block 54, an uncertainty description may be received, including, for example, the energy bounds for the noise in the concentrations observations, model error and error in the initial condition.

In block 56, an a priori estimate may be developed as a preliminary estimate of the fluid flow velocity. The measured concentrations, uncertainty information, and a priori estimate may be assimilated into a reactive transport model, in block 58, and a solution to the corresponding partial differential equations may be found, in block 60, resulting in an a posteriori estimate of the average fluid flow velocity.

In block 62, an uncertainty estimate may be produced regarding the estimated velocity. For example, a statistical uncertainty estimate may include an ellipsoidal uncertainty description.

An example of a specific reactive transport model that may be implemented in an embodiment of a method for inferring the average velocity of a flowing fluid mixture from observed concentrations of a reacting constituent of the fluid may be exemplified assuming the concentration, C(t,x), is advected by the velocity field, u(t) that is uniform in space:

$$\partial_t C + u(t)\partial_x C - K(u)C = e(x,t),\ C(0,x) = C_0 + e^b(x) \qquad (3)$$

where $C_0$ is a given initial concentration, e is the model error and $e^b$ models an error in the initial condition.

For example, a minimax flow estimation may be derived from observations, or measurements, of constituent concentration, assuming the relationship between the measurement readings, $Y_s^k$, and the concentration, C(t,x), is given in the following form:

$$Y_s^k = \int_{\Omega_T} g_s^k(x,t) C(t,x)\, dx\, dt + \eta_s^k,\ k=\overline{1,M},\ s=\overline{1,S}, \qquad (4)$$

where $g_s^k$ encapsulates the gauge and $\eta_s^k$ stands for the observation noise, assuming that the domain $\Omega$ is approximated by a grid $\{(x_k)\}_k^N$ and the observed value of the concentration $C(t,x):\Omega_T \to [0,+\infty)$ on the k-grid cell at time $t_s \in [t_0,T]$ is represented by a real number $Y_s^k \in [0,+\infty)$.

The minimax flow estimation solution further may assume that u(t) is a weak solution of the following equation:

$$u_t = A(t)u(t) + B(t)f(t) \quad (5a)$$

$$u(t_0) = f_0 \quad (5b)$$

where $f_0$ is an uncertain initial condition, f(t) is a model error and A, B are matrices the arise from the discretization.

The minimax estimate of the flow velocity may be determined given the observations, or readings, $Y_s^k$, and assuming that the uncertain parameters, $e^b$, e, $f_0$, and f, belong to the given bounded convex sets, respectively, as well as that $\eta_s^k$ are independent scalar random variables with zero mean and covariances $R_s^k$.

Specifically, the minimax estimate of the flow velocity may be constructed using the following iterative algorithm based on duality principle. Given an initial guess for the flow velocity u*, and sensor readings in accordance with equation (4), the minimax estimate $\hat{C}^*$ of the concentration C*, corresponding to u* through equation (3), may be constructed using classical methods on state estimation for partial differential equations known in the art.

Having constructed the minimax estimate $\hat{C}^*$ as suggested above, one may differentiate it with respect to x to obtain the minimax estimate of $\partial_x \hat{C}^*$. The latter and u* may then be substituted into equation (3) ($\partial_x \hat{C}$ substitutes $\partial_x C$ and the reaction term K may be evaluated at =u*) and a system of linear equations for C and u results. For this system the minimax estimate of u and C may be constructed again using sensor readings in accordance with equation (4). Repeating these steps—that is, estimating the concentration for a fixed flow velocity, u*, computing the gradient of the estimated concentration, $\partial_x \hat{C}$, plugging the gradient back into the equation (3), and again estimating the concentration and the flow velocity—comprises an iterative algorithm. This algorithm may be iterated until the obtained sequence of flow velocity estimates converges.

An embodiment of the method disclosed for inferring the average velocity of a flowing fluid mixture from observed concentrations of a reacting constituent of the fluid may provide significant advantages over some existing solutions. An embodiment may allow flow rate measurements, or observations, to be taken in existing system access locations that are not suited to invasive installations of measurement equipment. An embodiment may use concentration observation data that is already being collected for other purposes. An embodiment may permit reconstruction of the concentration gradient across a conduit when only sparse observations are provided. An embodiment may implement a flexible uncertainty description in the form of ellipsoids and may provide a guaranteed error estimate. An embodiment may utilize a posteriori discretization, that is, the optimal estimate is analytically derived and equations are directly discretized for optimal estimate, as opposed to seeking an estimate for the discretized problem.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks. The corresponding structures, materials, acts, and equivalents of all means or step plus function elements in the claims below are intended to include any structure, material, or act for performing the function in combination with other claimed elements as specifically claimed.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A computer-implemented method for estimating a fluid flow velocity with a volumetric flow measurement device, comprising:

receiving, with a processing device, a plurality of observations from the volumetric flow measurement device corresponding to a concentration of a constituent of a flowing fluid mixture; and computing, with the processing device, a final estimate of an average velocity of the flowing fluid mixture based at least in part on the observations so as to provide an estimate of the volumetric flow rate without necessitating a dedicated flow measurement device, wherein the constituent is undergoing a chemical reaction and the computing implements a reactive transport model comprising the following partial differential equation:

$$\frac{\partial C(x,t)}{\partial t} = -u(t)\frac{\partial C(x,t)}{\partial x} + K(u(t))C(x,t),$$

wherein u is the velocity of the flowing fluid mixture, $C(x,t)$ is the concentration of the reacting constituent at a location, x, and time, t, and the concentration decays according to the first order constant, K.

2. The method of claim 1, further comprising:

sensing a measured concentration of the reacting constituent at a location along a travel path of the flowing fluid mixture; and sending the measured concentration to the processing device, wherein the measured concentration is one of the observations.

3. The method of claim 1, further comprising generating an initial estimate of the average velocity of the flowing fluid mixture, wherein the final estimate further is based at least in part on the initial estimate.

4. The method of claim 3, further comprising receiving an estimate of the accuracy of the observations, wherein the final estimate further is based at least in part on the estimate.

5. The method of claim 1, wherein the constituent is chlorine and the flowing fluid mixture includes water.

6. A computer-implemented method for estimating a fluid flow velocity with a volumetric flow measurement device, comprising:

receiving, with a processing device, a plurality of observations from the volumetric flow measurement device corresponding to a concentration of a constituent of a flowing fluid mixture; and computing a final estimate of an average velocity of the flowing fluid mixture based at least in part on the observations so as to provide an estimate of the volumetric flow rate without necessitating a dedicated flow measurement device, wherein the constituent is undergoing chemical reaction and the computing implements a reactive transport model, wherein the reactive transport model comprises an iterative algorithm including the following partial differential equation:

$$\partial_t C + u(t)\partial_x C - K(u)C = e(x,t),\ C(0,x) = C_0 + e^b(x)$$

where $C_0$ is a given initial concentration, e is the model error and $e^b$ models an error in the initial condition, and the concentration decays according to a function of the velocity, $K(u)$.

* * * * *